x

US010238737B2

(12) United States Patent
Ben Arous et al.

(10) Patent No.: US 10,238,737 B2
(45) Date of Patent: Mar. 26, 2019

(54) ORAL ADMINISTRATION OF AT LEAST ONE PHARMACEUTICAL AND/OR ANTIGENIC ACTIVE SUBSTANCE

(71) Applicant: SOCIETE D'EXPLOITATION DE PRODUITS POUR LES INDUSTRIES CHIMIQUES SEPPIC, Paris (FR)

(72) Inventors: Juliette Ben Arous, Issy les Moulineaux (FR); Laurent Dupuis, Reims (FR); Jerome Gaucheron, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 15/509,284

(22) PCT Filed: Sep. 7, 2015

(86) PCT No.: PCT/FR2015/052364
§ 371 (c)(1),
(2) Date: Mar. 7, 2017

(87) PCT Pub. No.: WO2016/046464
PCT Pub. Date: Mar. 31, 2016

(65) Prior Publication Data
US 2017/0281755 A1 Oct. 5, 2017

(30) Foreign Application Priority Data
Sep. 23, 2014 (FR) ...................... 14 58966

(51) Int. Cl.
| A61K 39/00 | (2006.01) |
| A61K 45/06 | (2006.01) |
| A61K 31/47 | (2006.01) |
| A61K 39/12 | (2006.01) |
| A61K 39/395 | (2006.01) |
| A61K 39/39 | (2006.01) |
| A61K 47/32 | (2006.01) |
| A61K 47/34 | (2017.01) |
| A61K 47/36 | (2006.01) |
| A61K 9/107 | (2006.01) |
| A61K 47/38 | (2006.01) |
| A61K 9/00 | (2006.01) |
| A61K 38/38 | (2006.01) |
| A61K 39/02 | (2006.01) |
| A61K 39/17 | (2006.01) |
| A61K 47/14 | (2017.01) |
| A61K 47/44 | (2017.01) |

(52) U.S. Cl.
CPC ............ *A61K 39/39* (2013.01); *A61K 9/0053* (2013.01); *A61K 9/107* (2013.01); *A61K 38/385* (2013.01); *A61K 39/0005* (2013.01); *A61K 39/0291* (2013.01); *A61K 39/17* (2013.01); *A61K 47/14* (2013.01); *A61K 47/32* (2013.01); *A61K 47/34* (2013.01); *A61K 47/36* (2013.01); *A61K 47/38* (2013.01); *A61K 47/44* (2013.01); *A61K 2039/542* (2013.01); *A61K 2039/55511* (2013.01); *A61K 2039/55566* (2013.01)

(58) Field of Classification Search
CPC ........ A61K 45/06; A61K 39/39; A61K 39/00; C07D 405/06; C07D 405/10
See application file for complete search history.

(56) References Cited

U.S. PATENT DOCUMENTS

| 2001/0028884 A1 | 10/2001 | Poulet |
| 2004/0198904 A1 | 10/2004 | Braun et al. |
| 2010/0233196 A1 | 9/2010 | Dupuis et al. |

FOREIGN PATENT DOCUMENTS

| CN | 106075457 | * | 11/2016 |
| EP | 0 073 006 A2 | | 3/1983 |
| EP | 1 726 600 | * | 11/2006 |
| EP | 1 726 600 A1 | | 11/2006 |
| EP | 1726600 A1 | * | 11/2006 |
| WO | 96/00719 A1 | | 1/1996 |
| WO | 01/78688 A1 | | 10/2001 |

OTHER PUBLICATIONS

International Search Report, dated Nov. 26, 2015, from corresponding PCT application.

* cited by examiner

*Primary Examiner* — Barry A Chestnut
(74) *Attorney, Agent, or Firm* — Young & Thompson

(57) ABSTRACT

Disclosed is a gastro-resistant vector for the oral administration of at least one pharmaceutical and/or antigenic active substance including an aqueous phase (W) and an oily phase (O) in the form of a water-in-oil (W/O)-type emulsion wherein the aqueous phase includes at least one active principle and between 2 and 40 wt. % of a hydrophilic polymer that is insoluble in an aqueous phase of pH<6.5.

17 Claims, 1 Drawing Sheet

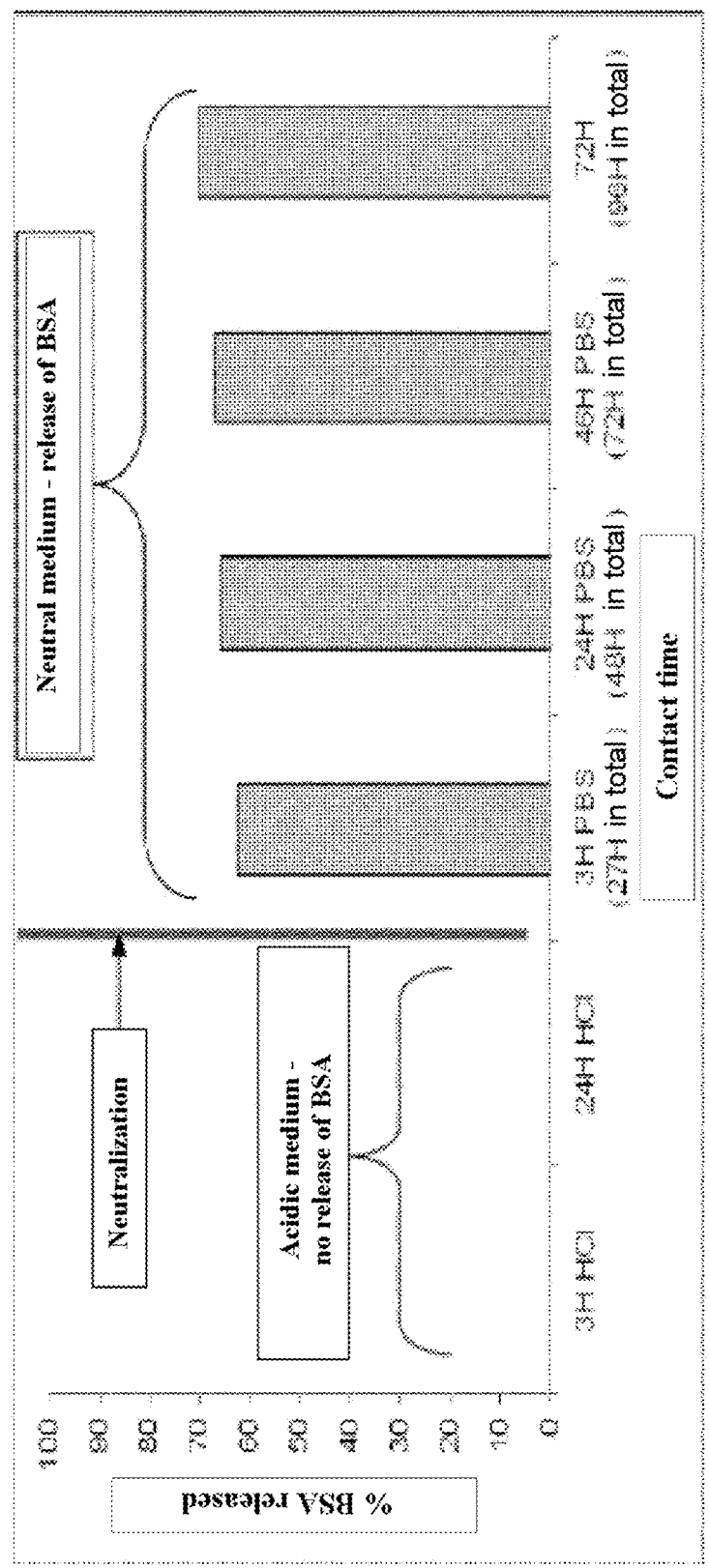

ORAL ADMINISTRATION OF AT LEAST ONE PHARMACEUTICAL AND/OR ANTIGENIC ACTIVE SUBSTANCE

BACKGROUND OF THE INVENTION

The present invention relates to a gastroresistant vector intended to be administered orally and containing at least one therapeutically and/or prophylactically active substance, to the use thereof and to the process for producing same.

Oral administration has many advantages for delivering medicaments and also vaccines. The bioavailability of an orally administered active ingredient is greatly reduced if the compound is degraded during its passage through the stomach regions that are generally rich in enzymes and are characterized by a very acidic pH. The purpose of the digestion mechanism is in fact to lyse a maximum number of chemical bonds so as to make macromolecules absorbable, by breaking them down into forms of smaller molecules. For large complex molecules, which medicinal active ingredients or vaccines generally are (in particular those based on proteins), this results in a loss of efficacy.

Nevertheless, for administering oral treatments, two major strategies exist for getting over the gastric barrier:
  administering large amounts of active ingredient: thus, even if a high proportion is degraded, an active part thereof will remain;
  carrying the active ingredient in an excipient that will protect it against degradation in the acidic stomach region and will release it in the effective region at neutral pH.

This second technique is referred to as placing in gastroresistant form. It is widely used in the form of gel capsules (which are filled with the active ingredient) or of tablets film-coated with at least one polymer film which is insoluble at acidic pH and soluble at neutral pH.

The filling of gel capsules and the film-coating of tablets are very complex, expensive industrial processes and do not make it possible to go down to administration units of very small size (the limiting size being that of the gel capsules and of the tablets). For film-coating, which can be envisioned for microgranules a few millimeters in diameter, this requires very specific, expensive equipment and processes for depositing gastroresistant films, requiring hot ventilation to evaporate off the solvent used to deposit the film on the moving support granules. This process is thus not usable for heat-sensitive active ingredients (such as, for example, vaccine antigens) and active ingredients of which the dust is toxic. Furthermore, it is virtually impossible, because of the filling and film-coating constraints, to work aseptically to produce sterile pharmaceutical products.

Liquid forms encapsulating hydrophilic active ingredients in oily matrices (for example water-in-oil emulsions) are used to "protect" and gradually release active ingredients and antigens by the injectable route (for example, the emulsion for oral administration of example 2 of patent EP 0 073 006), but do not withstand passage through the digestive system and are dissociated and destructured when they pass through the stomach.

Thickening polymer matrices ensuring the formation of a very slowly disintegrating tablet provide, through this gradual release, a gastroresistant effect, as described in patent application WO 2001/078688. If the matrix dissolution kinetics are calculated over the stomach/intestine transit time, the end fraction, which is released in the intestine, has crossed the stomach barrier, whereas the initial fraction, dissolved in the stomach, has been digested. The term delayed-effect matrix is used rather than true gastroresistance. In this case, the matrix must be large in size (for example, a tablet to be injected orally) to be adjusted according to the transit kinetics, the transit kinetics being variable according to recipient species, food bolus, age, type of digestion (fish, ruminants, etc.). The performance levels of matrices of this type are variable.

Polymer macromolecules, in order to be used in oral formulations, must be soluble at neutral pH: this is because the release of the active ingredients is thus ensured. The largest molecules (high-molecular-weight polymers) give the best protection during passage through the acidic regions. However, these polymers all have the drawback of causing the viscosity of aqueous solutions to increase, converting them into gel or semi-solids that cannot be poured, are difficult to quantitatively determine and difficult to absorb.

Gastroresistant polymers cannot be used directly at a high content in aqueous solutions since the high viscosity that they develop prevents flow. Moreover, it is known that the gels of these polymers, at acidic pH, form a precipitate of said polymer.

These precipitates, put back to a neutral pH, make it possible to release the molecules trapped during the precipitation of the polymers.

BRIEF DESCRIPTION OF THE INVENTION

For this reason, the inventors of the present invention have sought to develop a solution which makes it possible to solve the previously identified problems.

A subject of the present invention is thus a gastroresistant vector suitable for the oral administration of at least one pharmaceutical and/or antigenic active substance comprising an aqueous phase (W) and an oily phase (O) in the form of an emulsion of water-in-oil (W/O) type wherein the aqueous phase comprises at least one active ingredient and from 2% to 40% by weight of hydrophilic polymer that is insoluble in an aqueous phase at pH<6.5.

A subject of the invention is also:

A vector as defined above, characterized in that the oily phase comprises at least one surfactant and at least one oil chosen from fatty acid esters, a fluid mineral oil, a vegetable oil and squalane.

A vector as defined above, characterized in that the oil chosen is ethyl oleate.

A vector as defined above, characterized in that said hydrophilic polymer is chosen from polysaccharides consisting solely of monosaccharides, polysaccharides consisting of monosaccharide derivatives, cellulose derivatives and polymers of polyelectrolyte type.

A vector as defined above, characterized in that the hydrophilic polymer is chosen from hydroxypropylmethylcellulose acetate succinate, hydroxypropylmethyl cellulose phthalate, cellulose acetate phthalate, shellac, copolymers of methacrylic acid and of methyl methacrylate, dimethylaminoethyl methacrylate, and butyl methacrylate.

A vector as defined above, characterized in that said hydrophilic polymer is chosen from derivatives of acrylamide, of acrylic acid and of vinylpyrrolidone, such as copolymers of acrylic acid and of 2-methyl-[(1-oxo-2-propenyl) amino]-1-propanesulfonic acid (AMPS), copolymers of acrylamide and of 2-methyl-[(1-oxo-2-propenyl)amino]-1-propanesulfonic acid, copolymers of 2-methyl-[(1-oxo-2-propenyl)amino]-1-propanesulfonic acid and of (2-hydroxyethyl) acrylate, the homopolymer of 2-methyl-[(1-oxo-2-propenyl)amino]-1-propanesulfonic acid, the homopolymer of acrylic acid, copolymers of acryloylethyltrimethylammonium chloride and of acrylamide, copolymers of AMPS and of vinylpyrrolidone, copolymers of acrylic acid and of alkyl acrylates of which the carbon-based chain comprises between ten and thirty carbon atoms, and copolymers of AMPS and of alkyl acrylates of which the carbon-based chain comprises between ten and thirty carbon atoms.

A vector as defined above, comprising an immunity adjuvant chosen from sodium polyacrylate, alginates, a microemulsion, and divalent salts.

A vector as defined above, characterized in that the active ingredient is a substance capable of being denatured or degraded during direct oral administration and is chosen from an antigen, a medicament, an antiparasitic and an antibiotic.

A vector as defined above, characterized in that the amount of said hydrophilic polymer added is greater than 4% by weight of the final composition and less than 20% by weight and preferably between 10% by weight and 20% by weight of the final composition.

A gastroresistant carrier comprising one or more vectors as defined above.

A composition comprising at least one vector as defined above or a carrier as defined above.

The use of a vector as defined above or a carrier as defined above for obtaining a medicament that is active orally in human or veterinary therapy and that has curative and/or preventive properties and/or properties enabling diagnosis.

The use as defined above, for producing a pharmaceutical and/or veterinary product intended for oral vaccination.

A process for preparing a vector as defined above, comprising the following steps:

a) preparing an oily phase comprising one or more oils, and an emulsifying system, comprising one or more emulsifying surfactants and at least one hydrophilic polymer that is insoluble in an aqueous phase at pH<6.5 and optionally water for stabilizing the vector;

b) adding water containing the active ingredient to be made gastroresistant, with stirring, in order to form an emulsion of water-in-oil (W/O) type comprising at least 10% by weight of water.

A process as defined above, characterized in that the aqueous phase (W) of the emulsion of water-in-oil (W/O) type contains an active ingredient which is a substance capable of being denatured or degraded during direct oral administration and is chosen from an antigen, a medicament, an antiparasitic and an antibiotic.

A process as defined above, wherein said polymer is added in step a) in the form of oily reverse latex.

A process as defined above, wherein said polymer is added in step a) in the form of powder to be dispersed in water.

A process as defined above, wherein said polymer is added in step a) in the form of a liquid aqueous dispersion or of an organic solution to be emulsified in the starting oily composition.

A process as defined above, wherein the steps take place at a temperature below 55° C. and preferably between 5° C. and 35° C.

A pharmaceutical or veterinary preparation comprising a vector prepared by means of the process defined above.

BRIEF DESCRIPTION OF THE DRAWINGS

FIG. 1 represents the release test of BSA. The graph shows the release rate of BSA for 24h in acid medium then for 72h in neural medium. The vertical line separates these two periods.

DETAILED DESCRIPTION OF THE INVENTION

By combining the oily liquid vector technique with high concentrations of gastroresistant hydrophilic polymer in the emulsified aqueous phase, the inventors of the present invention have succeeded in formulating a novel excipient which makes it possible to obtain a pourable fluid emulsion of water-in-oil type. In addition, the drops of water dispersed in this emulsion contain high contents of hydrophilic polymers. Moreover, the gastroresistant hydrophilic polymers (which are insoluble and precipitate at acidic pH but are soluble at neutral pH) do not thicken the emulsion since they thicken each drop independently.

Very surprisingly, it is possible to incorporate high contents of hydrophilic polymers, without thickening the emulsion, by means of a mixing process.

The preparation of the gel emulsion in gastroresistant oil is carried out as follows:

1/ An oily excipient containing an oil plus a surfactant system is formulated to give, after addition of approximately 30% of water, a fluid and stable emulsion of water-in-oil (W/O) type (example of oil: ethyl oleate, fluid mineral oil, vegetable oil, squalane) (example of surfactant: Montanide™ 888, Montanide™ 80, Montane™ 80+Montanox™ 80 pair).

2/ In this oily excipient, the hydrophilic polymer (i.e. hydrophilic polymer obtained by carrying out a radical polymerization process in water-in-oil emulsion, for instance the reverse latexes (sold under the trade names Simulgel™ and Sepigel by SEPPIC) or polymer powder (obtained either by carrying out a radical precipitation polymerization process in a suitable solvent, for instance the hydrophilic polymers sold under the trade name Carbopol™ and Eudragit™, or by carrying out a radical polymerization process in water-in-oil emulsion followed by a step of precipitating the hydrophilic polymer from a suitable solvent or by a spray-drying step) is dispersed with vigorous stirring, added in the form, for example, of oily reverse latex (for example Simulgel™ and Sepigel™ sold by SEPPIC) or of powder (for example Carbopol™, Eudragit™). The amount of polymer added may be high (2% to 20% by weight in the final formula), without however modifying the viscosity of the oily mixture.

3/ The aqueous phase of the emulsion, containing the active agent (antigen, medicament, antiparasitic, antibiotic) is gradually added with stirring. The formula is thus completed.

During the addition of the aqueous phase containing the active ingredient, the drops form, with the dispersed hydrophilic polymer particles, small gelled particles (drops of emulsion of approximately one micrometer in diameter). These drops contain the active ingredient to be protected, trapped in a semi-solid aggregate composed of the hydrated hydrophilic polymer.

During the use of this fluid emulsion for oral distribution (for example, a spoonful of this liquid poured onto foods for chickens or for fish), the emulsion will become destructured (emulsions of water-in-oil (W/O) type are destroyed by the digestion mechanisms). Polymer aggregates will thus be released and, at acidic pH, will become insoluble, causing a precipitation that strongly traps the active ingredient to be carried, thereby protecting it from the destructive external medium. Once gastric transit has finished, the passing into neutral medium will allow dissolution of the polymers, becoming diluted in the intestinal fluids and releasing the active ingredient. The use of immunity adjuvants for mucosal vaccination (sodium polyacrylate, alginates, microemulsion, divalent salts) combined with this gastroresistant matrix also makes it possible to increase the immune response in the case of oral vaccination.

According to the present invention, the fatty phase comprises one or more oils chosen in particular from:

oils of vegetable origin, such as sweet almond oil, coconut oil, monoï oil, castor oil, jojoba oil, olive oil, rapeseed oil, peanut oil, sunflower oil, wheat germ oil, corn germ oil, soybean oil, cottonseed oil, alfalfa oil, poppyseed oil, pumpkin oil, evening primrose oil, millet oil, barley oil, rye oil, safflower oil, candlenut oil, passionflower oil, hazelnut oil, palm oil, shea butter, apricot kernel oil, calophyllum oil, sisymbrium oil, avocado oil, calendula oil;

vegetable oils and ethoxylated methyl esters thereof;

oils of animal origin, such as squalene or squalane;

mineral oils, such as liquid paraffin, liquid petroleum jelly and isoparaffins;

synthetic oils, in particular fatty acid esters, such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, lanolic acid-derived esters, such as isopropyl lanolate, isocetyl lanolate, fatty acid monoglycerides, diglycerides and triglycerides such as glyceryl triheptanoate, alkyl benzoates, poly-alpha-olefins, polyolefins such as polyisobutene, synthetic isoalkanes such as isohexadecane and isododecane and perfluoro oils. Silicone oils can also be used in the context of the present invention.

Among the latter, mention may more particularly be made of dimethylpolysiloxanes, methylphenylpolysiloxanes, amine-modified silicones, fatty acid-modified silicones, alcohol-modified silicones, silicones modified with alcohols and fatty acids, silicones modified with polyether groups, epoxy modified silicones, silicones modified with fluoro groups, cyclic silicones and silicones modified with alkyl groups. However, for practical reasons, it may be desirable for the fatty phase not to comprise silicone oil.

The water-in-oil emulsion generally comprises from 20% to 80% by weight, preferably from 30% to 70% by weight, of oil.

Among the emulsifying surfactants that can be used in the context of the present invention, mention will in particular be made of N-acyl amino acids and salts thereof; lipopeptides and salts thereof; sorbitan esters, for instance the product sold under the name Montane™ 80 by the company SEPPIC; polyglycerol esters, for instance the products sold under the name Isolan™ GI34 by BASF and Plurol™ Diisostearic by Gattefosse; ethoxylated castor oil and ethoxylated hydrogenated castor oil, for instance the product sold under the name Simulsol™ 989 by the company SEPPIC; glyceryl stearate; polyglycol polyhydroxystearates or polyglycerol polyhydroxystearates, for instance the products called Hypermer™ B246, Arlacel™ P135 sold by the company Uniqema, the product called Dehymuls™ PGPH sold by the company Cognis, the product called Decaglyn™ 5HS sold by the company Nikko; polyethylene glycol-alkyl glycol copolymers, for instance the PEG-45 dodecyl glycol copolymer, such as the product sold under the name Elfacos ST 9™ by the company Akzo, ethoxylated sorbitan esters, for instance the products sold under the name Montanox™ by the company SEPPIC; weakly ethoxylated protein acrylates (from 1 to 3 OE groups); ethoxylated beeswax, for instance the product called Apifil® sold by the company Gattefosse; cationic emulsifiers such as amine oxides, quaternium 82 and the surfactants described in patent application WO 96/00719 and mainly those of which the fatty chain comprises at least 16 carbon atoms; sucrose esters, methylglucoside esters which may or may not be ethoxylated; ethoxylated fatty acids; ethoxylated fatty alcohols; anionic emulsifiers such as decyl phosphate or cetearyl sulfate; aluminum polyoxystearate, for instance the product sold under the name Manalox® by the company Rhodia; magnesium stearate; aluminum stearate.

Among the linear, branched and/or crosslinked polyelectrolyte-type polymers, which are most particularly suitable for implementing the process of the present invention, mention may be made of derivatives of acrylamide, of acrylic acid and of vinylpyrrolidone, such as copolymers of acrylic acid and of 2-methyl-[(1-oxo-2-propenyl)amino]-1-propanesulfonic acid (AMPS), copolymers of acrylamide and of 2-methyl-[(1-oxo-2-propenyl)amino]-1-propanesulfonic acid, copolymers of 2-methyl-[(1-oxo-2-propenyl) amino]-1-propanesulfonic acid and of (2-hydroxyethyl) acrylate, the homopolymer of 2-methyl-[(1-oxo-2-propenyl) amino]-1-propanesulfonic acid, the homopolymer of acrylic acid, copolymers of acryloylethyltrimethylammonium chloride and of acrylamide, copolymers of AMPS and of vinylpyrrolidone, copolymers of acrylic acid and of alkyl acrylates of which the carbon-based chain comprises between ten and thirty carbon atoms, and copolymers of AMPS and of alkyl acrylates of which the carbon-based chain comprises between ten and thirty carbon atoms.

Such polymers are generally prepared by means of a reverse-phase radical polymerization process, and are in particular sold respectively under the names Simulgel™ EG, Sepigel™ 305, Simulgel™ NS, Simulgel™ 800 and Simulgel™ A by the company SEPPIC. They involve partially or totally salified forms of the monomers bearing an acid function. The corresponding monomer(s) is (are) dissolved in drops of water dispersed in a fatty phase by means of an emulsifying surfactant system. Such polymers can also be prepared by means of a radical precipitation polymerization process; the corresponding monomer(s) is (are) dissolved in a solvent in which the polymer formed is insoluble and precipitates at the end of the polymerization reaction, which is followed by a phase of filtering and drying the polymer powder obtained.

Advantageously, the dry weight of said polyelectrolyte constitutes between 0.1% and 4% and preferably between 0.5% and 2% of the weight of the aqueous phase, if the process for preparing such a polyelectrolyte results from a precipitation polymerization process; or the dry weight of said polyelectrolyte constitutes between 0.25% and 4% and preferably between 0.5% and 2% of the weight of the aqueous phase if the process for preparing such a polyelectrolyte results from an inverse emulsion polymerization preparation process.

Below are examples of oily excipients for an emulsion of water-in-oil type.

The oily adjuvants are diverse in nature.

Freund's adjuvants, which are the oldest, result from the combination of a white mineral oil resulting from the distillation of petroleum and of a mannitol ester optionally containing a killed *mycobacterium*.

The commercial oily adjuvants sold under the name Montanide™ ISA have the advantage of producing emulsions of water-in-oil (W/O) type, termed fluid, having viscosities of about 500 mPa·s measured using a Brookfield LVT viscometer equipped with a No. 2 spindle rotating at a speed of 60 revolutions per minute.

The international patent application published under number WO 99/20305 discloses the use of surfactants on mannitol oleate with mineral oils such as Marcol™ 52 for producing "fluid" emulsions.

Other than the ready-to-use commercial oily adjuvants which contain one or more oils and one or more surfactants, it is possible to use sorbitol esters (Span™) and ethoxylated sorbitol esters (Tween™) by the vaccine manufacturer itself.

These surfactants in combination with one or more oils are commonly used to produce emulsified vaccine compositions of water-in-oil W/O type.

Example of Preparation by Addition of Polymer

The composition of the gastroresistant oily adjuvant used here is an optimized mixture of a reverse latex of sodium polyacrylate (SPA), of Montanide ISA and of water. The reverse latex of SPA is the dispersion of the polymer in an oily matrix during the radical polymerization reaction making it possible to obtain it.

Example:
50% reverse latex of SPA
20% Montanide™ ISA
30% water.

Another possible method can be to dope an emulsion of water-in-oil W/O type specifically formulated with powdered polymer (for example a carbomer such as Carbopol™ 971 or 940 or other grade) which is dispersed with vigorous mechanical stirring so as to create the basic emulsion which has a high polymer load.

All the chemical structures of polymers that are insoluble at acidic pH (<6), the viscosity of the aqueous gel of which drops by at least 50% and the solubility of which decreases when the pH goes from 7 to 2, can be used for formulations of this type.

Chemically, these various families of thickeners can be classified as follows:
Polysaccharides consisting only of monosaccharides.
Polysaccharides consisting of monosaccharide derivatives.
Cellulose derivatives.
Linear or branched and/or crosslinked polyelectrolyte-type polymers.

Mention will be made for example of the following polymers:
In the form of powders (to be redispersed in the water of the formulation of the gastroresistant oily vector (EHGR)): hydroxypropylmethylcellulose acetate succinate, for example Agoat™ from Shin Etsu, hydroxypropylmethylcellulose phthalate, for example HP50™ and HP55™ from Shin Etsu, cellulose acetate phthalate, shellac, for example Shellac™, copolymers of methacrylic acid and of methyl methacrylate, for example Eudragit™ L100 and Eudragit™ S100 from Evonik, PVAP, for example Sureteric from Colorcon, dimethylaminoethyl methacrylate, butyl methacrylate, and copolymers of methyl methacrylate, for example: Eudragit E100™ from Evonik.
In the form of a liquid aqueous dispersion (to be emulsified in the EHGR: ethylcellulose, for example Aquacoat™ from FMC, polymethacrylate formulated with PEG8000, for example Acryl Eze™ from Colorcon, polymethacrylate in an aqueous dispersion at 30%, for example Eudragit L30D™.
In the form of an organic dispersion or solution (to be emulsified in the EHGR): methacrylic acid copolymers of methyl methacrylate in isopropyl alcohol, for example Eudragit™ S12.5 from Evonik.
Or in the form of a dispersion of polymer in a water-in-oil emulsion (reverse latex or inverse emulsion) (this time to be diluted in the EHGR), for example the Sepigel™ and Simulgel™ product ranges from SEPPIC.

Demonstration of the Gastroresistance Properties In Vitro

The gastroresistant oily excipient (or vector) (EHGR) of formula below is emulsified using a mixer with a strong dispersing power (such as a Silverson L4RT) by mixing 70% by weight of the EHGR with 30% by weight of a solution of model protein BSA.

50% reverse latex of SPA.
20% Montanide™ ISA.
30% water.

Final composition:
70% of oily vector.
30% aqueous medium containing the active agent to be made gastroresistant (for example: BSA).

Final Composition of the Gastroresistant Emulsion Tested with Respect to Gastroresistant Capacity The concentration is 4 mg of BSA per gram of emulsion of water-in-oil (W/O) type in the final mixture.

A release test is carried out in two steps using the Erweka dissolution apparatus with 600 g of recipient medium and 60 g of emulsion with stirring at 100 rpm (protocol extracted from the pharmacopeia recommendations).

The emulsion is firstly placed in an acid solution (0.1M HCl) for 24 hours and then the pH of this solution is brought back up to neutral pH and the solution is evaluated for 72 hours.

The results of this experiment are shown in FIG. 1.

There was no release of BSA over the course of one day in acid medium (0.1M HCl). Approximately 75% of BSA was released over the course of three days in neutral medium (PBS, pH=7.2).

The objective of the acid medium is to mimic the passage through the stomach and the objective of the neutral medium is to mimic the passage through the intestine.

These results demonstrate the gastroresistant nature of the preparation: indeed, the encapsulated active ingredient (in this case BSA) is not released in acidic medium (close to 0%), but is released (approximately 75%) when it passes into neutral medium. The presence of assayable BSA indicates that the protein was protected against degradation during the passage in acidic medium.

These same tests were carried out with two other types of polymers dispersed in the EHGR:
Sepigel™ 501 (crosslinked copolymer, in reverse latex form, of acrylamide and of sodium acrylate, dispersed in a mineral liquid paraffin).
Eudragit™ L100-55 (anionic polymer having functional methacrylic acid groups).

The results are presented in table 1 in comparison with the previous test carried out with sodium polyacrylate.

TABLE 1

In vitro results of gastroresistance property measured on EHGR compositions obtained from various polymers

|  | Sodium polyacrylate in dispersion (reverse latex) | Sepigel ™ 501 (reverse latex) | Eudragit ™ L100 (powder) |
|---|---|---|---|
| BSA encapsulated in EHGR |  | 4 mg/g of EHGR |  |
| Fraction released after 24 hours in 0.1M HCl | 0 | 0 | 0 |
| Fraction released after 72 hours pH brought back up to 7 | 75% | 86% | 82% |

These formulations exhibit strong gastroresistance for polymers of different chemical structures and introduced into the composition in various forms (powder and reverse latex).

Demonstration of Gastroresistance Properties In Vivo

Three animal models were tested to demonstrate the effectiveness of the vectors according to the present invention in animal applications:

1/ Mice: After anesthesia, mice were administered, by gavage, 100 µl of this EHGR preparation containing 10 mg of model protein (ovalbumin: OVA) in comparison with an aqueous solution. The immunological responses measured in the feces proved to be very significantly greater for the group having swallowed the EHGR compared with the group having swallowed the aqueous solution. This thus indicates that the protein was indeed intact when it reached the immunocompetent system of the digestive system located after the stomach (Peyer's patches) without being degraded, whereas the ovalbumin in solution was digested in the stomach (cf. table 2).

TABLE 2

Assays of the anti-OVA antibodies in the feces of mice after gavage with 10 mg of OVA/mouse

| Anti-OVA antibody (feces) (EU/ml) | T0 | 30 DAYS (D) | 60 D | 90 D |
|---|---|---|---|---|
| Control group (no ova) | 0 | 0 | 0 | 0 |
| OVA in aqueous solution | 0 | 0 | 0 | 0 |
| OVA in EHGR | 0 | 100 | 200 | 200 |

The values of 100 and 200 obtained when the EHGR excipient "vectorizes" the OVA are very high and indicate a strong immune response. The EHGR is thus clearly an adjuvant for oral vaccination.

2/ Fish: A *Yersinia* antigen was prepared in the EHGR in comparison with an aqueous solution and was poured onto food tablets before distribution to farmed fish (rainbow trout). The protection induced (measured by virulent challenge) was clearly greater for the group having swallowed the EHGR compared with the group having swallowed the aqueous solution. The group having swallowed the aqueous solution behaved like the unvaccinated negative control group (cf. table 3).

TABLE 3

Impact of the excipient on the protection induced by oral vaccination with the Yersinia antigen on rainbow trout

|  | Vaccination D 0 | Virulent challenge D 30 | Lesion scores D 45 |
|---|---|---|---|
| Control groups (no antigen) | No antigen/1000 fish | Addition of bacteria to the bath | +++ |
| Antigen in solution | 100 ml/1000 fish | Addition of bacteria to the bath | +++ |
| Antigen in EHGR | 100 ml of antigens formulated in EHGR for 1000 fish | Addition of bacteria to the bath | No lesions |

The use of the EHGR makes the oral vaccination protective against the disease (no lesion), whereas the control groups do not withstand the infection.

3/ Hens: Newcastle disease antigen was administered orally to groups of 20 one-week-old hens. The vaccines, placed in the drinking water, were formulated in EHGR or in aqueous solution. The antibody titers measured in the serum and the mortality are evaluated in this test.

The antigen administered in aqueous solution did not provide any detectable antibody production and the animals exhibited the symptoms of the disease (mortality) similar to the control group which had received nothing.

The group having received the preparation of the antigen in EHGR exhibits detectable antibody titers and was protected against the infection during the virulent challenge (cf. table 4).

TABLE 4

Results of protections induced by the Newcastle disease antigen after oral administration (drinking water) in the form of gastroresistant vector or of aqueous solution. Only the group having received the antigen vectorized by the EHGR is protected against the disease and exhibits antibody titers.

|  | Vaccination D 0 | Serum antibodies | Survivors after virulent challenge (%) |
|---|---|---|---|
| Control groups (no antigen) | No antigen | Not detected | 7 |
| Antigen in solution | 50 ml of antigen/20 hens | Not detected | 5 |
| Antigen in EHGR | 50 ml of antigen formulated in EHGR/20 hens | 4 log2 | 95 |

The invention claimed is:

1. A gastroresistant vector suitable for oral administration of at least one pharmaceutical and/or antigenic active substance comprising:
    an aqueous phase (W), and
    an oily phase (O),
said vector being in the form of an emulsion of water-in-oil (W/O) type,
    wherein the aqueous phase comprises at least one active ingredient and sodium polyacrylate, and
    wherein said vector comprises at least 10% by weight water, 20% to 80% by weight of oil, and from 2% to 40% by weight of sodium polyacrylate.

2. The vector as claimed in claim 1, wherein the oily phase comprises at least one surfactant and at least one oil chosen from fatty acid esters, a fluid mineral oil, a vegetable oil, and squalane.

3. The vector as claimed in claim 2, wherein the oil chosen is ethyl oleate.

4. The vector as claimed in claim 1, comprising an immunity adjuvant chosen from alginates, a microemulsion, and divalent salts.

5. The vector as claimed in claim 1, wherein the active ingredient is a substance capable of being denatured or degraded during direct oral administration and is chosen from an antigen, a medicament, an antiparasitic and an antibiotic.

6. The vector as claimed in claim 1, wherein the amount of said sodium polyacrylate added is greater than 4% by weight of the final composition and less than 20% by weight of the final composition.

7. A gastroresistant carrier comprising one or more vectors as claimed in claim 1.

8. A composition comprising at least one vector as defined in claim 1.

9. A medicament that is orally active in human or veterinary therapy and that has curative and/or preventive properties and/or properties enabling diagnosis, comprising the vector of claim 1.

10. A pharmaceutical and/or veterinary product intended for oral vaccination, comprising the medicament of claim 9.

11. A process for preparing a vector as defined in claim 1, comprising the following steps:
 a) preparing an oily phase comprising one or more oils, and an emulsifying system, comprising one or more emulsifying surfactants and sodium polyacrylate and optionally water for stabilizing the vector;
 b) adding water containing the active ingredient to be made gastroresistant, with stirring, in order to form an emulsion of water-in-oil (W/O) type comprising at least 10% by weight of water.

12. The process as claimed in claim 11, wherein the aqueous phase (W) of the emulsion of water-in-oil (W/O) type contains an active ingredient which is a substance capable of being denatured or degraded during direct oral administration and is chosen from an antigen, a medicament, an antiparasitic and an antibiotic.

13. The process as claimed in claim 11, wherein the sodium polyacrylate is added in step a) in the form of oily reverse latex.

14. The process as claimed in claim 11, wherein the sodium polyacrylate is added in step a) in the form of powder to be dispersed in the water.

15. The process as claimed in claim 11, wherein the sodium polyacrylate is added in step a) in the form of a liquid aqueous dispersion or of an organic solution to be emulsified in the starting oily composition.

16. The process as claimed in claim 11, wherein the steps take place at a temperature below 55° C.

17. The process of claim 16, wherein the steps take place at a temperature between 5° C. and 35° C.

* * * * *